United States Patent
Duperron et al.

(10) Patent No.: US 11,464,412 B2
(45) Date of Patent: Oct. 11, 2022

(54) BI-REFRINGENCE COMPENSATED WAVEGUIDES

(71) Applicant: Medlumics S.L., Madrid (ES)

(72) Inventors: Matthieu Duperron, Savigny-sur-Orge (FR); Juan Sancho Durá, Madrid (ES); José Luis Rubio Guivernau, Madrid (ES); Sara María Más Gómez, Santander (ES)

(73) Assignee: Medlumics S.L., Madrid (ES)

( * ) Notice: Subject to any disclaimer, the term of this patent is extended or adjusted under 35 U.S.C. 154(b) by 0 days.

(21) Appl. No.: 17/084,056

(22) Filed: Oct. 29, 2020

(65) Prior Publication Data

US 2021/0121069 A1 Apr. 29, 2021

Related U.S. Application Data

(63) Continuation of application No. 16/222,284, filed on Dec. 17, 2018, now Pat. No. 10,820,806.
(Continued)

(51) Int. Cl.
*A61B 5/00* (2006.01)
*G02B 6/122* (2006.01)
(Continued)

(52) U.S. Cl.
CPC .......... *A61B 5/0084* (2013.01); *A61B 5/0066* (2013.01); *A61B 5/6852* (2013.01);
(Continued)

(58) Field of Classification Search
None
See application file for complete search history.

(56) References Cited

U.S. PATENT DOCUMENTS 9,354,040 B2  5/2016  Rubio Guivernau et al.
9,366,885 B2  6/2016  Rubio Guivernau et al.
(Continued)

FOREIGN PATENT DOCUMENTS

JP  2009253129 A  10/2009

OTHER PUBLICATIONS

International Search Report and Written Opinion of the International Searching Authority directed to related International Patent Application No. PCT/EP2018/086380, dated Mar. 27, 2019; 11 pages.
(Continued)

*Primary Examiner* — Jerry Rahll
(74) *Attorney, Agent, or Firm* — Sterne, Kessler, Goldstein & Fox P.L.L.C.

(57) ABSTRACT

A medical instrument is described that includes an optical source, an optical fiber, and a waveguide patterned upon a substrate. The optical fiber receives radiation from the optical source and includes a first segment and a second segment. The second segment is rotated about an optical axis relative to the first segment. The waveguide receives radiation from the optical source and guides a beam of radiation. The waveguide includes a first waveguide segment designed to impart a first differential group delay on the beam of radiation and a second waveguide segment designed to impart a second differential group delay on the beam of radiation. A sum of the first differential group delay and the second differential group delay is substantially zero.

21 Claims, 7 Drawing Sheets

Related U.S. Application Data

(60) Provisional application No. 62/610,756, filed on Dec. 27, 2017.

(51) Int. Cl.

| | | |
|---|---|---|
| *G02B 6/126* | (2006.01) | |
| *G02B 6/024* | (2006.01) | |
| *A61B 90/00* | (2016.01) | |
| *G02B 6/12* | (2006.01) | |
| *A61B 90/30* | (2016.01) | |
| *G01B 9/02091* | (2022.01) | |
| *G01B 9/0209* | (2022.01) | |

(52) U.S. Cl.
CPC ............ *G02B 6/024* (2013.01); *G02B 6/126* (2013.01); *G02B 6/1228* (2013.01); *A61B 2090/306* (2016.02); *A61B 2090/3614* (2016.02); *G01B 9/0209* (2013.01); *G01B 9/02091* (2013.01); *G02B 2006/12061* (2013.01); *G02B 2006/12164* (2013.01)

(56) References Cited

U.S. PATENT DOCUMENTS

| | | | |
|---|---|---|---|
| 2001/0031942 | A1 | 10/2001 | Tollner et al. |
| 2003/0208252 | A1 | 11/2003 | O'Boyle et al. |
| 2006/0093276 | A1* | 5/2006 | Bouma .................... G02B 6/32 |
| | | | 385/72 |
| 2008/0089641 | A1 | 4/2008 | Feldchtein |
| 2008/0144991 | A1 | 6/2008 | Penninckx |
| 2009/0018393 | A1 | 1/2009 | Dick et al. |
| 2009/0306520 | A1 | 12/2009 | Schmitt et al. |
| 2010/0041986 | A1 | 2/2010 | Nguyen et al. |
| 2010/0046953 | A1 | 2/2010 | Shaw et al. |
| 2014/0078510 | A1* | 3/2014 | Rubio Guivernau ........................ |
| | | | G01B 9/02082 |
| | | | 356/479 |
| 2014/0118748 | A1 | 5/2014 | Rubio Guivernau et al. |
| 2014/0276682 | A1* | 9/2014 | Hendrick ................ A61M 1/84 |
| | | | 606/7 |
| 2014/0276683 | A1* | 9/2014 | Hendrick ............. A61B 18/245 |
| | | | 606/7 |
| 2014/0328556 | A1* | 11/2014 | Rubio Guivernau ........................ |
| | | | G02B 6/29376 |
| | | | 385/1 |
| 2015/0085293 | A1 | 3/2015 | Wang et al. |
| 2015/0209105 | A1 | 7/2015 | Margallo Balbás et al. |
| 2016/0038031 | A1 | 2/2016 | Margallo Balbás et al. |
| 2017/0027639 | A1* | 2/2017 | Margallo ............. A61B 5/0084 |
| 2017/0086860 | A1* | 3/2017 | Lee ........................ A61B 17/22 |
| 2019/0192005 | A1 | 6/2019 | Duperron et al. |

OTHER PUBLICATIONS

Fleming, Christine, et al., "Optical Coherence Tomography Imaging of Cardiac Radiofrequency Ablation Lesions," Poster presented at Biomedical Optics 2008, St. Petersburg, Florida, Mar. 16-19, 2008; 7 pages.

Fleming, Christine, et al., "Real-Time Imaging of Radiofrequency Cardiac Ablation Using Optical Coherence Tomography," OSA Technical Digest (CD) (Optical Society of America, Mar. 2008), paper BMD88, Mar. 2008; 3 pages.

Boppart, Stephen A., et al., "Real-Time Optical Coherence Tomography for Minimally Invasive Imaging of Prostrate Ablation," Computer Aided Surgery 6:94-103, Accepted Feb. 2001, published online Jan. 2010; 10 pages.

Patel, Nirlep A., et al., "Guidance of Aortic Ablation Using Optical Coherence Tomography," The International Journal of Cardiovascular Imaging 19:171-178, Apr. 2003; 8 pages.

De Boer, Johannes F., et al., "Two-Dimensional Birefringence Imaging in Biological Tissue Using Polarization Sensitive Optical Coherence Tomography," SPIE vol. 3196, 0277, pp. 32-37, Jan. 1998; 6 pages.

Everett, M.J., et al., "Birefringence Characterization of Biological Tissue by Use of Optical Coherence Tomography," Optics Letters, vol. 23, No. 3, Feb. 1, 1998; 3 pages.

Fleming, Christine, "Characterization of Cardiac Tissue Using Optical Coherence Tomography," Department of Biomedical Engineering, Case Western Reserve University, May 2010; 210 pages.

\* cited by examiner

BI-REFRINGENCE COMPENSATED WAVEGUIDES

CROSS-REFERENCE TO RELATED APPLICATIONS

This application is a continuation of U.S. application Ser. No. 16/222,284, filed Dec. 17, 2018, which claims the benefit of U.S. Provisional Application No. 62/610,756, filed Dec. 27, 2017, the disclosures of which are incorporated by reference herein in their entireties.

TECHNICAL FIELD

Embodiments of the application relate to waveguides having designs aimed at compensating for bi-refringence effects.

BACKGROUND

Low coherence interferometry (LCI) is often used in the medical imaging field to provide depth-resolved information of both internal and external tissue. Example LCI techniques include optical coherence reflectometry (OCR) and optical coherence tomography (OCT), which can each provide depth resolved information with high axial resolution by means of a broadband light source and an interferometric detection system.

When using these LCI imaging techniques with medical devices, the devices often require optical links to deliver light between a light source and the target sample, and between the sample and a detector. One problem with many of these optical links is that they exhibit the optical property of bi-refringence. In these bi-refringent optical links, the propagating medium/waveguide presents a different refractive index for the different polarization states of light propagating along it, causing a differential group delay (DGD) between light components on each of the polarization states. Whenever an interface between two bi-refringent optical links occurs within a system, very precise alignment between the optical axis of both links is needed in order to prevent cross-talk between polarization components that have accumulated a DGD.

Alignment precision when connecting optical links is often limited by mechanical or process-related tolerances. Typical angular tolerances range from ±3° for standard precision to ±1° for high precision connections. When a misalignment occurs at an interconnection of two optical links, the extinction ratio measuring the portion of light which goes into the undesired axis on the receiving link can be calculated as $ER=10*\log_{10}(\tan^2 \theta)$, where $\theta$ is the angular misalignment on the interconnection. ER values corresponding to the above-mentioned ±3° and ±1° are 25.6 dB and 30.2 dB, respectively. While these values might be good enough for many applications, for high dynamic range measuring techniques like OCR and OCT, where the imaging dynamic range can be as high as 40-50 dB, those values of ER are not enough for ensuring that there are no measurement artifacts due to the cross-coupled polarization components.

BRIEF SUMMARY

In the embodiments presented herein, different optical waveguide devices for reducing detrimental effects on an optical signal due to accumulated DGD are described.

In an embodiment, a catheter system includes a catheter, a processing device, and an optical fiber disposed in the processing device, or between the processing device and the catheter, or within a sheath of the catheter. The catheter includes a proximal section, a distal section, and the sheath connecting the proximal section to the distal section. The distal section includes a substrate having one or more waveguides patterned upon the substrate. A first waveguide of the one or more waveguides is designed to guide a beam of radiation. The processing device includes an optical source designed to generate a source beam of radiation and a communications interface designed to transmit electrical and optical signals to the proximal section of the catheter. The optical fiber includes a first segment and a second segment. The second segment is rotated about an optical axis relative to the first segment.

In another embodiment, an optical integrated circuit includes a substrate and a waveguide patterned upon the substrate. The waveguide guides a beam of radiation and includes a first waveguide segment designed to impart a first differential group delay on the beam of radiation, a second waveguide segment designed to impart a second differential group delay on the beam of radiation, and a coupling region between the first and second waveguide segments. A sum of the first differential group delay and the second differential group delay is substantially zero.

In another embodiment, a medical instrument includes an optical source, an optical fiber, and a waveguide patterned upon a substrate. The optical fiber receives radiation from the optical source and includes a first segment and a second segment. The second segment is rotated about an optical axis relative to the first segment. The waveguide receives radiation from the optical source and guides a beam of radiation. The waveguide includes a first waveguide segment designed to impart a first differential group delay on the beam of radiation and a second waveguide segment designed to impart a second differential group delay on the beam of radiation. A sum of the first differential group delay and the second differential group delay is substantially zero.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Described herein are embodiments of a medical device, such as a catheter, that uses optical signals to visualize the placement and/or movement of the device within a patient's body. Low coherence interferometry (LCI) may be used with the optical signals to provide depth-resolved information about the sample tissue being imaged. Although portions of the application may focus on catheters and the transmittance of optical signals through parts of the catheters, it should be understood that the embodiments discussed herein may apply to any medical device that utilizes optical signals. Furthermore, embodiments herein relating to reducing or eliminating the effect that the differential group delay (DGD) has on the information extracted from the optical signals may be used in any system or device that transmits and/or receives light for the purpose of measurement or analytical study.

Herein, the terms "electromagnetic radiation," "light," and "beam of radiation" are all used to describe the same electromagnetic signals propagating through the various described elements and systems.

Catheter Embodiments

Figure 1:
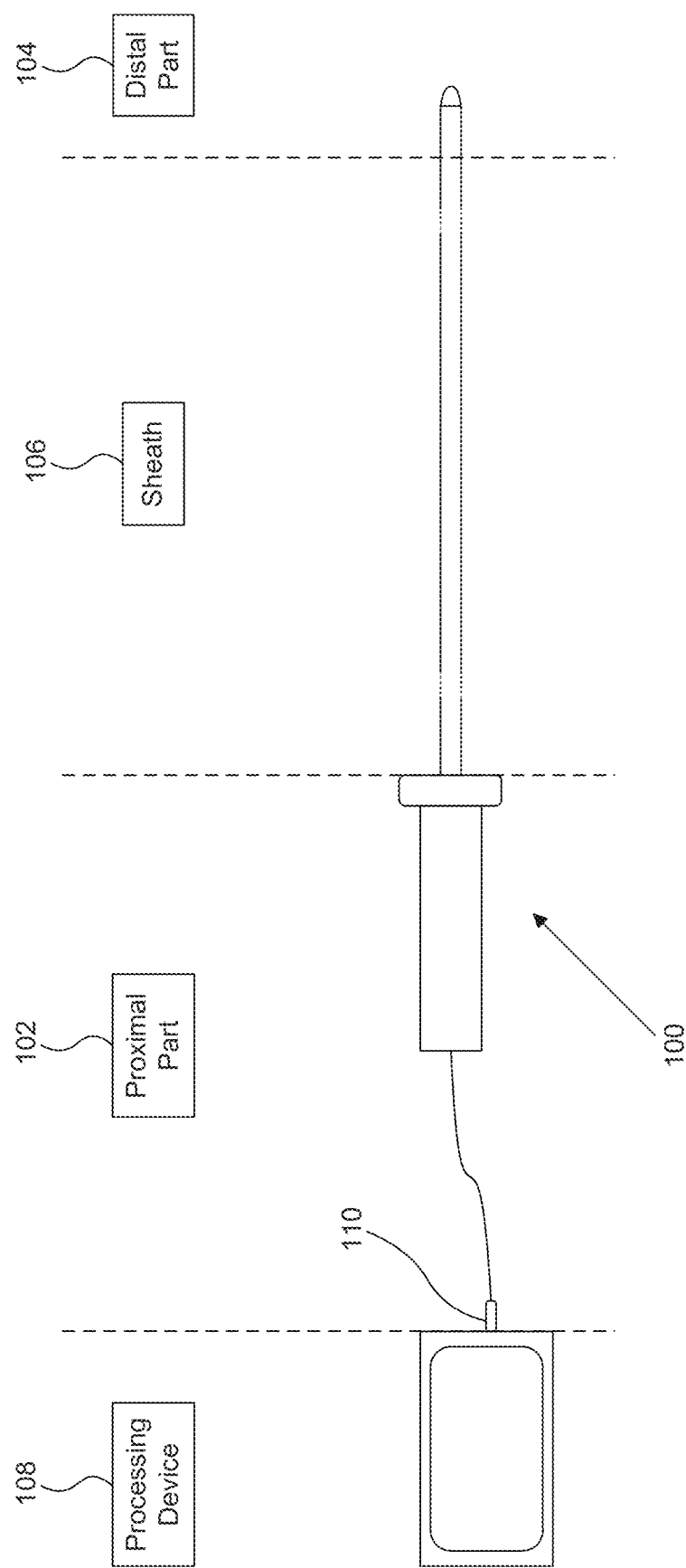
FIG. 1 illustrates a catheter, according to an embodiment.

FIG. 1 illustrates a catheter 100 according to an embodiment. Catheter 100 includes a proximal part 102, a distal part 104, and a sheath 106 coupled between proximal part 102 and distal part 104. In an embodiment, sheath 106 includes one or more radiopaque markers for navigation purposes. In one embodiment, catheter 100 includes a communication interface 110 between catheter 100 and a processing device 108. Communication interface 110 may include one or more wires and/or optical patch cords between processing device 108 and catheter 100. In other examples, communication interface 110 is an interface component that allows wireless communication, such as Bluetooth, WiFi, cellular, etc. Communication interface 110 may communicate with one or more transceiver elements located within either proximal part 102 or distal part 104 of catheter 100.

In an embodiment, sheath 106 and distal part 104 are disposable. As such, proximal part 102 may be reused by attaching a new sheath 106 and distal part 104 each time a new procedure is to be performed. In another embodiment, proximal part 102 is also disposable.

Proximal part 102 may house various electrical and optical components used in the operation of catheter 100. For example, a power supply may be included within proximal part 102 to apply RF energy to an electrode located at distal part 104 for tissue ablation. The power supply may be designed to generate an alternating current at frequencies at least between 350 and 500 kHz. As such, one or more conductive wires (or any electrical transmission medium) may lead from the power supply to distal part 104 within sheath 106. Furthermore, proximal part 102 may include an optical source for generating a beam of radiation.

In another embodiment, various electrical and optical components such as the power supply, optical source, and interferometer elements are located in processing device 108. Optical signals may be transferred between the optical source and interferometer elements using optical fibers within processing device 108. The electrical and optical signals from these components may be sent to proximal part 102 via communication interface 110. By housing these components in processing device 108, the whole of catheter 100 may be disposable.

The optical source may include one or more laser diodes or light emitting diodes (LEDs). The beam of radiation generated by the optical source may have a wavelength within the infrared range. In one example, the beam of radiation has a central wavelength of 1.3 µm. The optical source may be designed to output a beam of radiation at only a single wavelength, or it may be a swept source and be designed to output a range of different wavelengths. The range of wavelengths may include any wavelengths found in the near-infrared or mid-infrared spectral range. The generated beam of radiation may be guided towards distal part 104 via an optical transmission medium connected between proximal part 102 and distal part 104 within sheath 106. Some examples of optical transmission media include single mode and multimode optical fibers and integrated optical waveguides. In one embodiment, the electrical transmission medium and the optical transmission medium are provided by the same hybrid medium allowing for both electrical and optical signal propagation.

In an embodiment, proximal part 102 or processing device 108 includes one or more components of an interferometer in order to perform LCI using the light generated from the optical source. Further details of the LCI system are discussed with reference to FIG. 3. Due to the nature of interferometric data analysis, in an embodiment the optical transmission medium used for guiding the light to and from distal part 104 does not affect the state and degree of light polarization. In another embodiment, the optical transmission medium affects the polarization in a constant and reversible way.

Proximal part 102 may include further interface elements with which a user of catheter 100 can control the operation of catheter 100. For example, proximal part 102 may include a deflection control mechanism that controls a deflection angle of distal part 104. The deflection control mechanism may require a mechanical movement of an element on proximal part 102, or the deflection control mechanism may use electrical connections to control the movement of distal part 104. Proximal part 102 may include various buttons or switches that allow a user to control when RF energy is applied at distal part 104, or when the beams of radiation are transmitted from distal part 104, allowing for the acquisition of optical data. In some examples, these buttons or switches are located at a separate user interface coupled to processing device 108.

Distal part 104 may include one or more external electrodes for ablation, according to some embodiments. Distal part 104 may also include a plurality of optical view ports to transmit/collect light at various angles from distal part 104. Distal part 104 may include a substrate with patterned waveguides for guiding light to/from each of the plurality of optical view ports. The substrate may be a flexible (including a partially flexible) substrate made from a material such as polyimide, polyethylene glycol, Parylene, or polydimethelsiloxane (PDMS).

The optical view ports may be distributed over the outside of distal part 104, resulting in a plurality of distinct viewing directions, according to an embodiment. In an embodiment, each of the plurality of viewing directions is substantially non-coplanar.

Figure 2A:
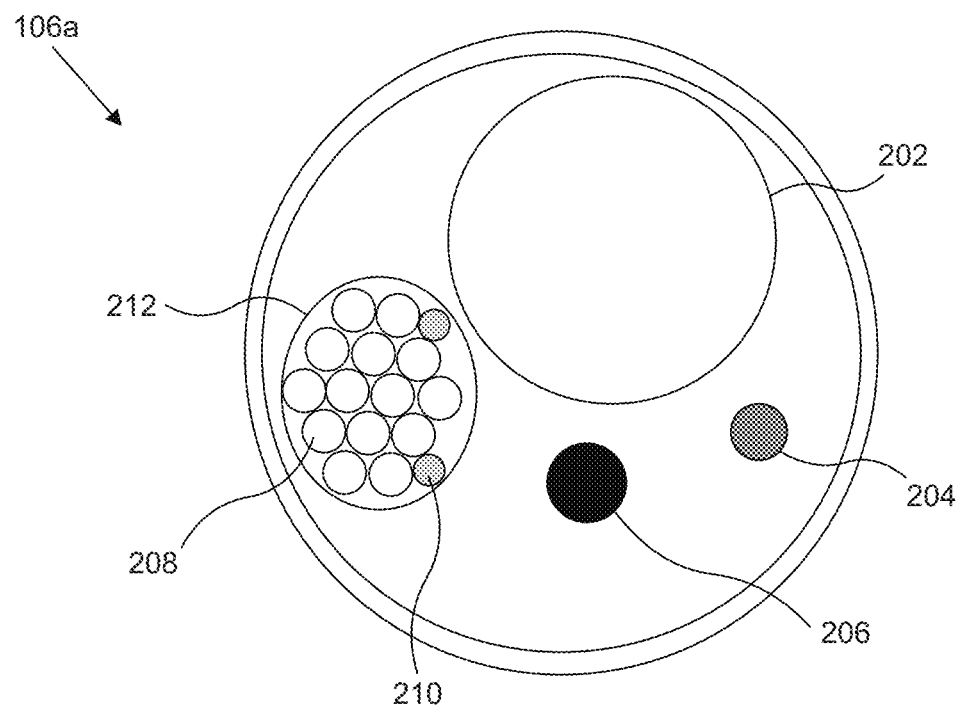
FIGS. 2A-2B illustrate cross sections of a catheter, according to embodiments.
Figure 2B:
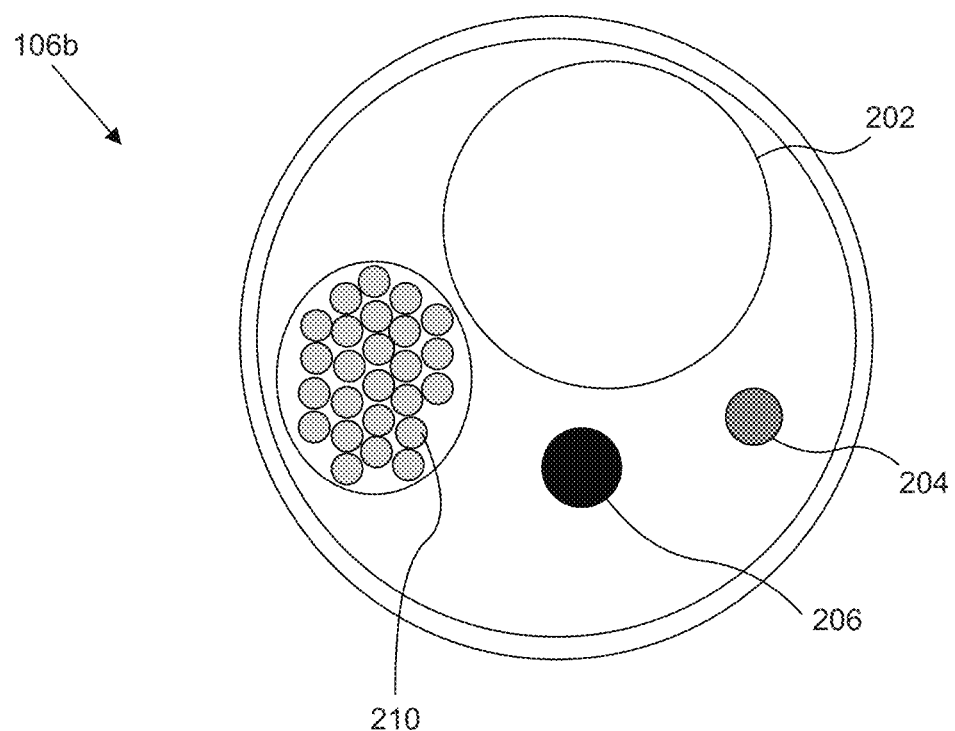

FIGS. 2A and 2B illustrate cross-section views of sheath 106, according to embodiments. Sheath 106 may include all of the elements interconnecting proximal part 102 with distal part 104. Sheath 106a illustrates an embodiment that houses an irrigation channel 202, RF conductive medium 204, deflection mechanism 206, electrical connections 208, and optical transmission media 210. RF conduction medium 204 and irrigation channel 202 may not be necessary if catheter 100 is not being used for ablation. FIG. 2A illustrates a protective cover 212 wrapped around both electrical connections 208 and optical transmission media 210. Electrical connections 208 may be used to provide signals to optical modulating components located in distal part 104. One or more optical transmission media 210 guide light generated from the optical source (exposure light) towards distal part 104, while another subset of optical transmission media 210 guides light returning from distal part 104 (scattered or reflected light) back to proximal part 102. In another example, the same one or more optical transmission media 210 guides light in both directions. According to an embodiment, optical transmission media 210 include polarization maintaining (PM) fibers.

Deflection mechanism 206 may include electrical or mechanical elements designed to provide a signal to distal part 104 in order to change a deflection angle of distal part 104. The deflection system enables guidance of distal part 104 by actuating a mechanical control placed in proximal part 102, according to an embodiment. This system may be based on a series of aligned and uniformly spaced cutouts in sheath 106 aimed at providing unidirectional deflection of distal part 104, in combination with a wire which connects the deflection mechanism control in proximal part 102 with the catheter tip at distal part 104. In this way, a certain movement of the proximal part may be projected to the distal part. Other embodiments involving the combination of several control wires attached to the catheter tip may enable the deflection of the catheter tip along different directions.

FIG. 2B illustrates a cross-section of sheath 106b. Sheath 106b depicts an embodiment having most of the same elements as sheath 106a from FIG. 2A, except that there are no electrical connections 208. Sheath 106b may be used in situations where modulation (e.g., multiplexing) of the generated beam of radiation is performed in proximal part 102 or in processing device 108.

Further details of an ablation catheter that may utilize the embodiments described herein can be found in co-pending U.S. Patent Publication No. 2015/0209105, the disclosure of which is incorporated by reference herein in its entirety.

LCI System

Figure 3:
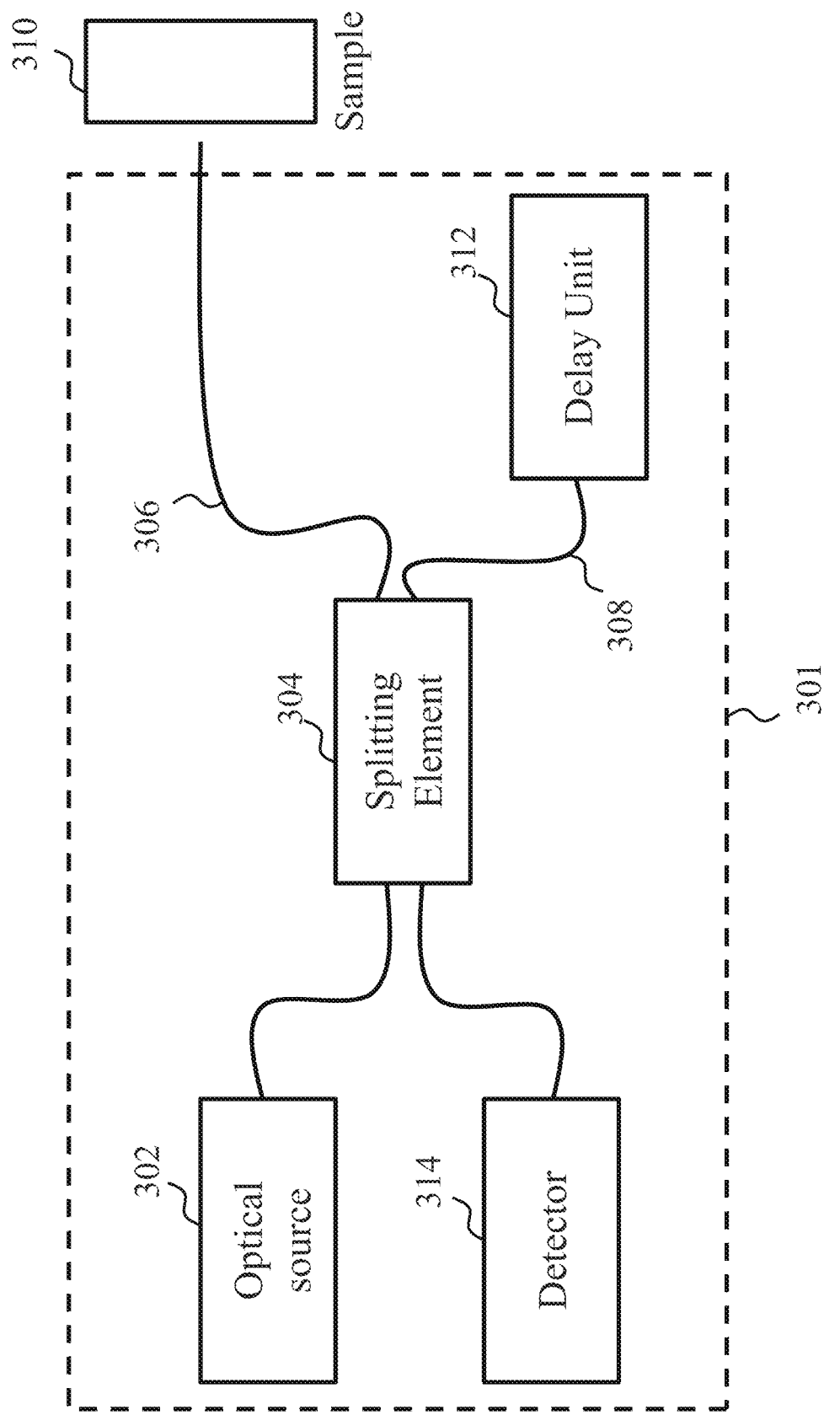
FIG. 3 illustrates a block diagram of a LCI system, according to an embodiment.

Various embodiments of the present application include a LCI system integrated within a medical device such as catheter 100 for optical interrogation of a sample. FIG. 3 illustrates an example LCI system 301 for imaging a sample 310, according to an embodiment. For example, sample 310 may be a tissue surface within a patient's body. A delay unit 312 may include various light modulating elements. These modulating elements may perform phase and/or frequency modulation to counteract undesired optical effects in the light, and to select one or more depths of sample 310 to be imaged. The use of the term "light" may refer to any range of the electromagnetic spectrum. In an embodiment, the term "light" refers to infrared radiation at a wavelength of about 1.3 µm.

LCI system 301 further includes an optical source 302, a splitting element 304, a sample arm 306, a reference arm 308, and a detector 314. In the embodiment shown, delay unit 312 is located within reference arm 308. However, it should be understood that delay unit 312 may instead be located in sample arm 306. Alternatively, various elements of delay unit 312 may be present in both sample arm 306 and reference arm 308. For example, elements of delay unit 312 that introduce a variable delay to the light may be located in sample arm 306, while elements that modulate different polarization modes of the light may be located in reference arm 308. In another example, elements of delay unit 312 that modulate different polarization modes of the light may be located in sample arm 306, while elements that introduce a variable delay to the light may be located in reference arm 308. In one example, sample arm 306 and reference arm 308 are optical waveguides, such as patterned waveguides or optical fibers. In an embodiment, all of the components of LCI system 301 are integrated onto a planar lightwave circuit (PLC). In another embodiment, at least the components within delay unit 312 are integrated on the same substrate of a PLC. Other implementations may be considered as well, such as, for example, fiber optic systems, free-space optical systems, photonic crystal systems, etc.

In an embodiment, delay unit 312 and splitting element 304 are integrated on a PLC while optical source 302 and detector 314 are provided separately from the PLC. In this embodiment, light may be coupled from optical source 302 to splitting element 304 via one or more PM fibers, and light may be coupled from splitting element 304 to detector 314 via one or more PM fibers or by direct free-space coupling.

It should be understood that LCI system 301 may include any number of other optical elements not shown for the sake of clarity. For example, LCI system 301 may include mirrors, lenses, gratings, splitters, micromechanical elements, etc., along the paths of sample arm 306 or reference arm 308.

Splitting element 304 is used to direct light received from optical source 302 to both sample arm 306 and reference arm 308. Splitting element 304 may be, for example, a bi-directional coupler, an optical splitter, an adjustable splitting-ratio coupler, or any other modulating optical device that converts a single beam of light into two or more beams of light.

Light that travels down sample arm 306 ultimately impinges upon sample 310. Sample 310 may be any suitable sample to be imaged, such as tissue. The light scatters and reflects back from various depths within sample 310 and the scattered/reflected radiation is collected back into sample arm 306. In another embodiment, the scattered/reflected radiation is collected back into a different waveguide than the transmitting waveguide. The scan depth may be chosen via the delay imposed on the light within delay unit 312.

Light within sample arm 306 and reference arm 308 is recombined before being received at detector 314. In the embodiment shown, the light is recombined by splitting element 304. In another embodiment, the light is recombined at a different optical coupling element than splitting element 304. Detector 314 may include any number of photodiodes, charge-coupling devices, and/or CMOS structures to transduce the received light into an electrical signal. The electrical signal contains depth-resolved optical data related to sample 310 and may be received by a processing device for further analysis and signal processing procedures. As used herein, the term "depth-resolved" defines data in which one or more portions of the data related to specific depths of an imaged sample can be identified.

In an embodiment, optical source 302, detector 314 and delay unit 312 are located within proximal part 102 of catheter 100. In another embodiment, optical source 302, detector 314 and delay unit 312 are located within processing device 108. Splitting element 304 and at least part of one or both of sample arm 306 and reference arm 308 may be located in processing device 108 or in either proximal part 102 or distal part 104 of catheter 100. In another embodiment, all of the elements of LCI system 301 are located in distal part 104 of catheter 100. Optical source 302 may include one or more light emitting diodes (LEDs) or laser diodes. For example, LEDs may be used when performing time domain and/or spectral domain analysis, while tunable lasers may be used to sweep the wavelength of the light across a range of wavelengths. In another embodiment, any of the components of LCI system 301 are located external to catheter 100, for example, within processing device 108.

LCI system 301 is illustrated as an interferometer design similar to a Michelson interferometer, according to an embodiment. However, other interferometer designs are possible as well, including Mach-Zehnder or Mireau interferometer designs.

PM Fiber Designs

As discussed above, medical devices such as catheters may use optical fibers to transmit and receive light. These optical fibers may include a PM fiber designed to maintain a given polarization state of the incident light as the light propagates through the PM fiber. With reference to FIG. 1, a PM fiber may be used within processing device 108, between processing device 108 and catheter 100, or within sheath 106. Depending on how accurately light is coupled into the PM fiber, a beam of radiation propagating down the length of the PM fiber may accumulate a differential group delay (DGD), which causes cross-talk between the polarized components of the light as the light is coupled to another PM fiber or waveguide. This cross-talk will degrade the optical signal (e.g., cause double images) ultimately being detected, especially for systems utilizing sensitive measurement techniques like LCI.

Figure 4:
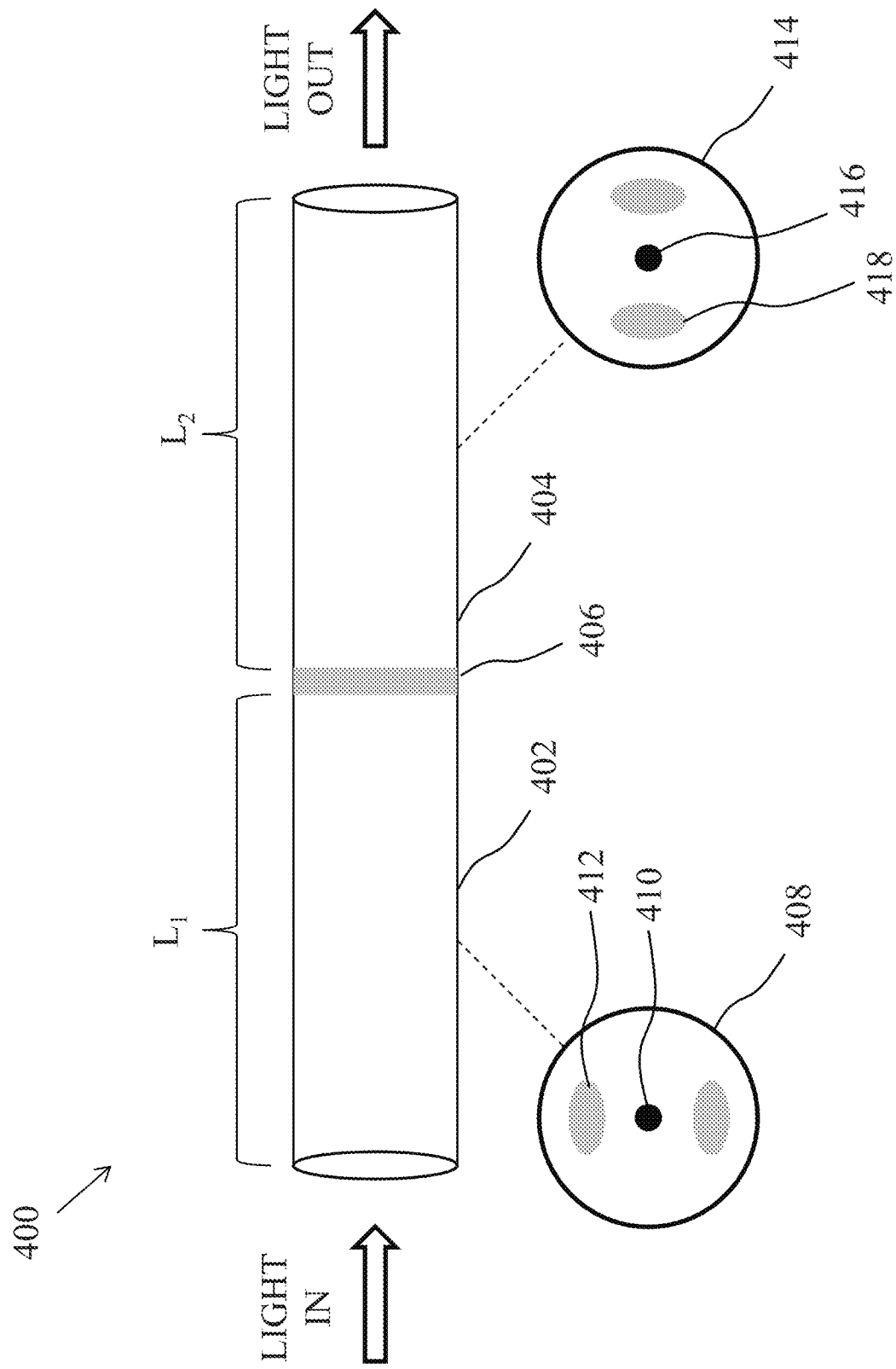
FIG. 4 illustrates a cross-spliced optical fiber, according to an embodiment.

According to an embodiment, a PM fiber design is provided to substantially negate any DGD introduced into the beam of radiation propagating through a PM fiber. FIG. 4 illustrates an example PM fiber 400 having a first segment 402 identified by a first length ($L_1$) and a second segment 404 identified by a second length ($L_2$), according to an embodiment. Light may be coupled into PM fiber 400 on one end and exit PM fiber 400 at the other end. The light exiting PM fiber 400 may be received by either a sample to be imaged, or by other optical components, such as additional waveguides.

Because PM fiber 400 maintains a given polarization state of the propagating beam of radiation, the fiber includes regions to introduce a non-uniform stress within the cladding surrounding the fiber core. Cross-section 408 illustrates a cross-section of first segment 402 having a first fiber core 410 and first stress-inducing regions 412. First fiber core 410 may have a diameter between about 2 microns and 9 microns. First stress-inducing regions 412 may be rods of a different material than the remainder of the cladding around first fiber core 410. Other shapes are designs of stress-inducing regions 412 may be used as would be understood to a person skilled in the relevant art.

According to an embodiment, second segment 404 is coupled to first segment 402 via a coupling region 406, and is rotated along an optical axis passing through the center of PM fiber 400 with respect to first segment 402. Cross-section 414 illustrates a cross-section of second segment 404 having a second fiber core 416 and second stress-inducing regions 418. Second fiber core 416 and second stress-inducing regions 418 may be the same as first fiber core 410 and first stress-inducing regions 412. In this example, second segment 404 is rotated 90° around the optical axis with respect to first segment 402. In other embodiments, second segment 404 may be rotated at any angle with respect to first segment 402. According to an embodiment, first segment 402 and second segment 404 have substantially the same length. The term "substantially" as it is used herein to pertain to length means that the lengths are close enough to one another so as to be insignificant with regards to any effect on the propagating beam of radiation.

By rotating two segments of a PM fiber of substantially equal length by 90°, any accumulated DGD on each of the polarization states will cancel out after the light has propagated through the entire length (i.e., $L_1+L_2$) of PM fiber 400, according to an embodiment. In other words, the light propagating through the "slow" polarization axis of first segment 402 accumulates a delay $DGD_1$ with respect to the light in the "fast" axis of the same first segment 402. The "slow" axis light from first segment 402 is then, thanks to the 90° rotation in the transition, coupled into the "fast" polarization axis of second segment 404, where it accumulates $-DGD_1$ with respect to the light propagating through the "slow" axis of second segment 404 which, thanks to the same 90° rotation in the transition, had previously propagated through the "fast" axis of first segment 402. As a result, the total DGD between the two polarization components entering PM fiber 400, as accumulated in PM fiber 400 as a whole, is $DGD_1-DGD_1=0$, or is substantially zero. The term "substantially zero" as it is used herein to pertain to DGD means that the DGD is small enough so as to be insignificant with regards to any effect on the propagating beam of radiation.

Coupling region 406 may represent a fusion splice between first segment 402 and second segment 404. Other coupling techniques may be used to couple first segment 402 and second segment 404, such as using an index-matching material between the two fiber segments or free space coupling with one or more lenses.

Although PM fiber 400 illustrates an example having only two segments of substantially equal length, in other embodiments, any number of fiber segments may be created with each segment characterized as having a given rotation about the optical axis. For example, multiple matching pairs of fiber segments may be spliced together. Furthermore, the fiber segments do not have to be the same length to cancel out the accumulated DGD. In some other embodiments, first segment 402 has a different propagation medium than second segment 404, such that the accumulated DGD per unit length of first segment 402 is different than the accumulated DGD per unit length of second segment 404. In these instances, the fiber segments may have different lengths to ultimately cancel the accumulated DGD.

Patterned Waveguide Designs

Embodiments of the present invention are not limited to optical fibers. Waveguides patterned on a substrate may also accumulate DGD in each of the polarization modes as light propagates down the length of the patterned waveguide, potentially causing the same problems discussed above.

Figure 5A:
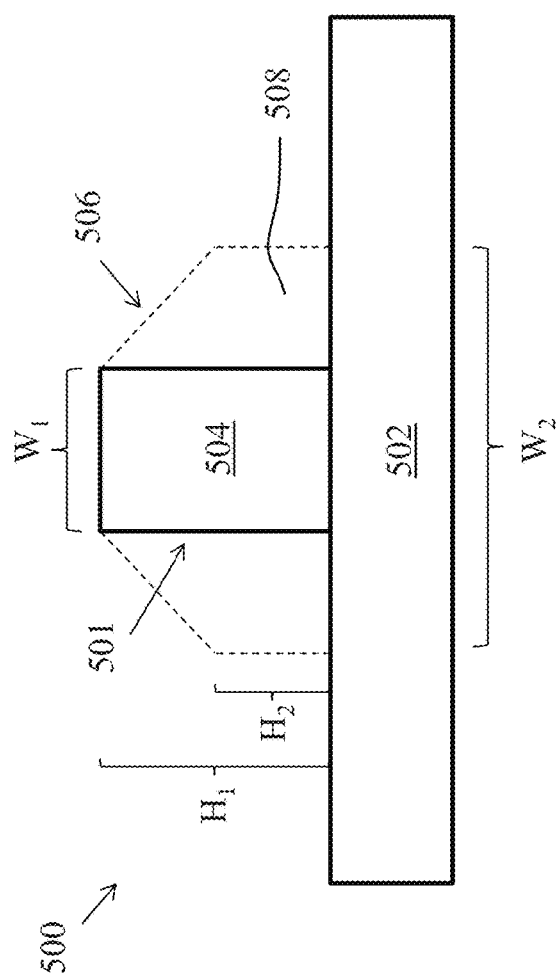
FIGS. 5A-5C illustrate different views of a patterned waveguide, according to some embodiments.
Figure 5B:
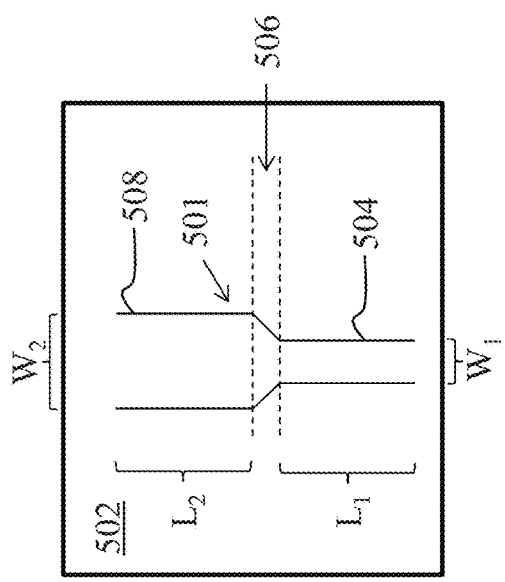
Figure 5C:
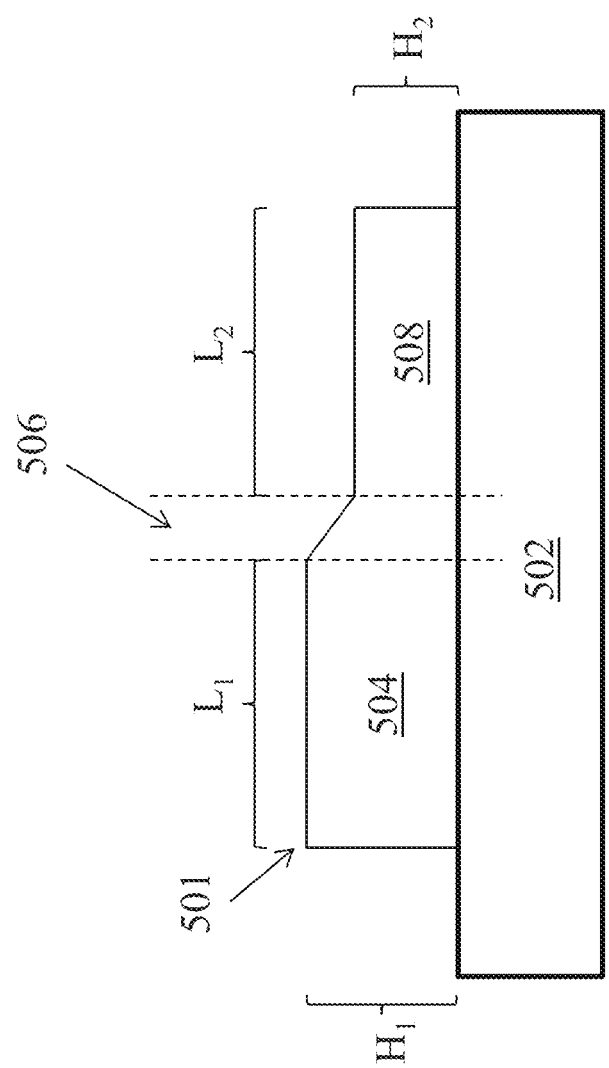

According to an embodiment, a patterned waveguide is designed to provide substantially zero accumulated DGD on the polarization modes of a propagating beam of radiation. FIGS. 5A-5C illustrate three views of an optical integrated circuit 500 that includes a waveguide 501 patterned on a substrate 502, according to an embodiment. Waveguide 501 may include silicon as a core material. Substrate 502 may be a silicon substrate, or may be another semiconducting material such as gallium arsenide or indium phosphide. Substrate 502 may also be a glass substrate. In some embodiments, substrate 502 is flexible polymer, such as PDMS, polyimide, Parylene, or polyethylene glycol.

Optical integrated circuit 500 may include any number of waveguides and/or other optical elements. For example, optical integrated circuit 500 may include an optical multiplexer (not illustrated) for switching light between various outputs or an optical amplifier. Other modulating elements such as phase modulators, frequency modulators, and delay elements may be included as well. Further details regarding other optical components that may be included with waveguide 501 on optical integrated circuit 500 may be found in co-owned U.S. Pat. Nos. 9,366,885 and 9,354,040, the disclosures of which are incorporated by reference herein in their entireties.

FIG. 5A illustrates a cross-section view of waveguide 501 having a first waveguide segment 504 and a second waveguide segment 508, according to an embodiment. FIG. 5B illustrates a top-down view of the same waveguide 501. FIG. 5C illustrates a side view of the same waveguide 501. First waveguide segment 504 may be characterized as having a width $W_1$, a height $H_1$ and a length $L_1$ while second waveguide segment 508 may be characterized as having a width $W_2$, a height $H_2$, and a length $L_2$. In an embodiment, $W_1$ is different from $W_2$, and $H_1$ is different from $H_2$. In one example, width $W_2$ may be designed to be greater than width $W_1$ and height $H_1$ may be designed to be greater than height $H_2$. For example, width $W_1$ may be between about 1.0 µm and 2.0 µm and width $W_2$ may be between about 2.0 µm and 5.0 µm. Height $H_1$ may be between about 2.0 µm and 5.0 µm and height $H_2$ may be between about 1.0 µm and 2.0 µm. According to an embodiment, length $L_1$ is substantially equal to length $L_2$.

First waveguide segment 504 and second waveguide segment 508 may be coupled together via a coupling region 506 where the geometry of first waveguide segment 504 shifts to match the different geometry of second waveguide segment 508. Coupling region 506 may have any length required to smoothly transition waveguide 501 from the height $H_1$ of first waveguide segment 504 to the height $H_2$ of second waveguide segment 508 and from the width $W_1$ of first waveguide segment 504 to the width $W_2$ of second waveguide segment 508. In one example, coupling region 506 may have a height that tapers from the first height $H_1$ to the second height $H_2$, and a width that tapers from the second width $W_2$ to the first width $W_1$. In another example, coupling region 506 includes a step change between $H_1$ and $H_2$ rather than a gradual change in height. Coupling region 506 may be formed from the same material as first waveguide segment 504 and second waveguide segment 508. According to an embodiment, coupling region 506 is formed at the same time as first waveguide segment 504 and second waveguide segment 508.

Waveguide 501 may be formed via a variety of fabrication techniques known to those skilled in the relevant art. For example, a reaction ion etch (RIE) procedure may be used to etch a layer of silicon masked by a patterned photoresist layer to form waveguide 501. The patterned photoresist may also have a non-uniform height, such that the non-uniform height topography is transferred to the silicon layer as the etch proceeds through the thickness of the photoresist. In another example, two masking steps may be used: a first masking step to form the waveguide having a changing width in the coupling region from $W_1$ to $W_2$; and a second masking step to gradually or abruptly change the height in the coupling region between $H_1$ and $H_2$.

By changing the cross-section geometry of the two coupled waveguide segments of substantially equal length, any accumulated DGD on each of the polarization states of a beam of light propagating through waveguide 501 will cancel out after the light has propagated through the entire length (i.e., $L_1+L_2$) of waveguide 501, according to an embodiment. In other words, the light propagating through the "slow" polarization axis of first waveguide segment 504 accumulates a delay $DGD_1$ with respect to the light in the "fast" axis of the same first waveguide segment 504. The "slow" axis light from first waveguide segment 504 is then, thanks to the change in both width and height of the waveguide, coupled into the "fast" polarization axis of second waveguide segment 508, where it accumulates $-DGD_1$ with respect to the light propagating through the "slow" axis of second waveguide segment 508 which, thanks to the same change in geometry, had previously propagated through the "fast" axis of first waveguide segment 504. As a result, the total DGD between the two polarization components entering waveguide 501, as accumulated in waveguide 501 as a whole, is $DGD_1-DGD_1=0$, or is substantially zero.

Other modifications made to first waveguide segment 504 and second waveguide segment 508 are also possible to result in substantially zero accumulated DGD. For example, first waveguide segment 504 may have a different core refractive index than second waveguide segment 508, such that the accumulated DGD per unit length of first waveguide segment 504 is different than the accumulated DGD per unit length of second waveguide segment 508. In these instances, the waveguide segments may have different lengths to ultimately cancel the accumulated DGD. The refractive index of each waveguide segment may be altered via introducing a dopant material into a given waveguide segment, or by applying heat or stress to a given waveguide segment.

Example Optical Medical Device

Figure 6:
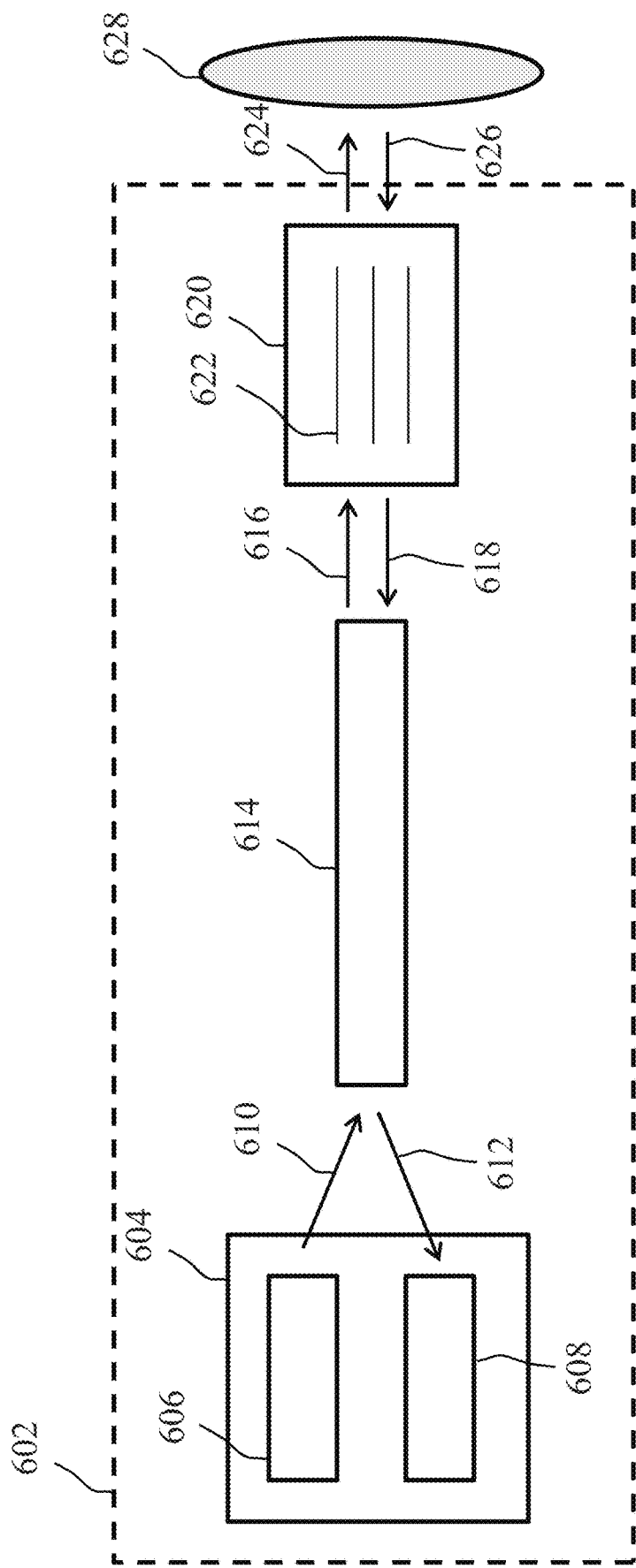
FIG. 6 illustrates an example optical system, according to an embodiment.

FIG. 6 illustrates an example of a medical device 602 that uses optical signals to interrogate a sample 628, according to an embodiment. Medical device 602 may include a processing module 604 that includes an optical source 606 and an optical detector 608. Processing module 604 may also include additional circuitry to measure the signal generated at optical detector 608 and use it to produce data that can be delivered to a user of medical device 602. The data may include visual information regarding sample 628 or material characteristics of sample 628 at a given depth. Processing module 604 may also include interferometer components used to perform LCI with the light received by optical detector 608. Optical source 606 and optical detector 608 may be similar to optical source 302 and detector 314 discussed above with reference to FIG. 3.

According to an embodiment, optical source 606 generates an incident beam of radiation 610 that is coupled into one or more PM fibers 614. One or more PM fibers 614 may have a design similar to that described for PM fiber 400, such that any accumulated DGD is substantially cancelled out by the time the light reaches the end of one or more PM fibers 614.

The light propagating through one or more PM fibers 614 exists as beam of radiation 616 where it is coupled into a waveguide 622 patterned on substrate 620, according to an embodiment. Waveguide 622 may have a design similar to that described for waveguide 501, such that any accumulated DGD due to coupling misalignment of beam of radiation 616 into waveguide 622 is substantially cancelled out by the time the light reaches the end of waveguide 622. Waveguide 622 may be one component of an optical integrated circuit formed on substrate 620. The optical integrated circuit may include any number of other waveguides and/or other optical elements. In one example, substrate 620 is a flexible (including a partially flexible) substrate that includes a polymer material. Example polymer materials include polyimide, polyethylene glycol, Parylene, or PDMS.

The light propagates through waveguide 622 and may propagate through one or more other waveguides before exiting from substrate 620 towards sample 628 as beam of radiation 624. Scattered or reflected radiation 626 is received from sample 628 back towards substrate 620 where it is coupled into one or more waveguides on substrate 620. The one or more waveguides that receive scattered or reflected radiation 626 may include the same waveguide 622.

The light received from the sample exits from substrate 620 as beam of light 618 that is coupled back into one or more PM fibers 614. Beam of light 618 may be coupled into the same one or more PM fibers used to propagate incident beam of radiation 610, or it may be coupled into different PM fibers. After traversing the length of one or more PM fibers 614, the light exits as beam of radiation 612 where it is received ultimately by an optical detector 608. In some embodiments, medical device 602 includes an optical interferometer such that the light returning from sample 628 is combined with light that traversed a separate reference path as discussed above with reference to FIG. 3. The light returning from sample 628 may be combined with the reference light either on substrate 620 or in processing module 604.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A catheter system, comprising:
   a catheter comprising:
      a proximal section,
      a distal section, and
      a sheath coupled between the proximal section and the distal section;
   a processing device comprising an optical source configured to generate a beam of radiation and a communications interface configured to transmit electrical and optical signals to the proximal section of the catheter; and
      an optical fiber provided in a substrate and disposed within the sheath, wherein the optical fiber comprises a first segment and a second segment, wherein the second segment of the optical fiber is rotated about an optical axis relative to the first segment of the optical fiber, and wherein the beam of radiation is propagated through the optical fiber and out the distal section of the catheter, wherein the first segment of the optical fiber is configured to impart a first differential group delay on the beam of radiation, the second segment of the optical fiber is configured to impart a second differential group delay on the beam of radiation, and a sum of the first differential group delay and the second differential group delay is substantially zero.

2. The catheter system of claim 1, wherein a propagation medium of the first segment is different from a propagation medium of the second segment, such that the first differential group delay per a length of the first segment is different from the second differential group delay per a length of the second segment.

3. The catheter system of claim 2, wherein the length of the first segment is different from the length of the second segment.

4. The catheter system of claim 1, wherein the optical fiber further comprises a coupling region between the first and second segments, wherein the coupling region comprises a fusion splice, an index-matching material, or a free space coupling with one or more lenses between the first and second segments.

5. The catheter system of claim 1, wherein a length of the first segment of the optical fiber is substantially equal to a length of the second segment of the optical fiber.

6. The catheter system of claim 1, wherein the optical fiber is a polarization maintaining fiber.

7. The catheter system of claim 6, wherein the second segment of the polarization maintaining fiber is rotated by 90 degrees relative to the first segment of the polarization maintaining fiber.

8. The catheter system of claim 1, wherein the distal section comprises a plurality of optical view ports in optical communication with the optical fiber and configured to transmit and collect light from a plurality of angles from the distal section.

9. A catheter comprising:
a proximal section,
a distal section,
a sheath coupled between the proximal section and the distal section, and
an optical fiber provided in a substrate and disposed within the sheath, wherein the optical fiber comprises a first segment and a second segment, wherein the second segment of the optical fiber is rotated about an optical axis relative to the first segment of the optical fiber, wherein the optical fiber is configured to receive a beam of radiation generated by an optical source and propagate the beam of radiation through the optical fiber and out the distal section, wherein the first segment of the optical fiber is configured to impart a first differential group delay on the beam of radiation, the second segment of the optical fiber is configured to impart a second differential group delay on the beam of radiation, and a sum of the first differential group delay and the second differential group delay is substantially zero.

10. The catheter of claim 9, wherein a propagation medium of the first segment is different from a propagation medium of the second segment, such that the first differential group delay per a length of the first segment is different from the second differential group delay per a length of the second segment.

11. The catheter of claim 10, wherein the length of the first segment is different from the length of the second segment.

12. The catheter of claim 9, wherein the optical fiber further comprises a coupling region between the first and second segments, wherein the coupling region comprises a fusion splice, an index-matching material, or a free space coupling with one or more lenses between the first and second segments.

13. The catheter of claim 9, wherein the optical fiber is a polarization maintaining fiber.

14. The catheter of claim 13, wherein the second segment of the polarization maintaining fiber is rotated by 90 degrees relative to the first segment of the polarization maintaining fiber.

15. The catheter of claim 9, wherein a length of the first segment of the optical fiber is substantially equal to a length of the second segment of the optical fiber.

16. The catheter of claim 9, wherein the distal section comprises a plurality of optical view ports in optical communication with the optical fiber and configured to transmit and collect light from a plurality of angles from the distal section.

17. A device comprising:
an optical source configured to generate a beam of radiation; and
a catheter comprising:
a proximal section,
a distal section,
a sheath coupled between the proximal section and the distal section; and
at least one optical fiber provided in a substrate and disposed within the sheath and coupled to the optical source, wherein the at least one optical fiber comprises a first segment and a second segment, wherein the second segment of the at least one optical fiber is rotated about an optical axis relative to the first segment, wherein the beam of radiation is propagated through the at least one optical fiber and out the distal section, wherein the first segment of the at least one optical fiber is configured to impart a first differential group delay on the beam of radiation, the second segment of the at least one optical fiber is configured to impart a second differential group delay on the beam of radiation, and a sum of the first differential group delay and the second differential group delay is substantially zero.

18. The device of claim 17, wherein a propagation medium of the first segment is different from a propagation medium of the second segment, such that the first differential group delay per a length of the first segment is different from the second differential group delay per a length of the second segment.

19. The device of claim 18, wherein the length of the first segment is different from the length of the second segment.

20. The device of claim 17, wherein the at least one optical fiber further comprises a coupling region between the first and second segments, wherein the coupling region comprises a fusion splice, an index-matching material, or a free space coupling with one or more lenses between the first and second segments.

21. The device of claim 17, wherein the distal section comprises a plurality of optical view ports in optical communication with the at least one optical fiber and configured to transmit and collect light from a plurality of angles from the distal section.

* * * * *

UNITED STATES PATENT AND TRADEMARK OFFICE
CERTIFICATE OF CORRECTION

PATENT NO.         : 11,464,412 B2
APPLICATION NO.    : 17/084056
DATED              : October 11, 2022
INVENTOR(S)        : Duperron et al.

Page 1 of 1

It is certified that error appears in the above-identified patent and that said Letters Patent is hereby corrected as shown below:

In the Specification

In Column 5, Lines 2-3, delete "polydimethelsiloxane" and insert -- polydimethylsiloxane --, therefor.

Signed and Sealed this
Twenty-seventh Day of August, 2024

Katherine Kelly Vidal
*Director of the United States Patent and Trademark Office*